(12) United States Patent
Pascal et al.

(10) Patent No.: US 9,426,984 B2
(45) Date of Patent: Aug. 30, 2016

(54) FUNGICIDAL AND PARASITICIDAL FIRE-RETARDANT POWDER

(75) Inventors: Jean-Philippe Pascal, Nancy (FR); Olivier Patat, Paris (FR); Magali Riglet, Viroflay (FR)

(73) Assignee: SOLVAY SA, Brussels (BE)

( * ) Notice: Subject to any disclaimer, the term of this patent is extended or adjusted under 35 U.S.C. 154(b) by 393 days.

(21) Appl. No.: 13/994,831

(22) PCT Filed: Dec. 22, 2011

(86) PCT No.: PCT/EP2011/073815
§ 371 (c)(1),
(2), (4) Date: Jun. 17, 2013

(87) PCT Pub. No.: WO2012/085218
PCT Pub. Date: Jun. 28, 2012

(65) Prior Publication Data
US 2013/0274347 A1 Oct. 17, 2013

(30) Foreign Application Priority Data

Dec. 22, 2010 (FR) ..................... 10 61057

(51) Int. Cl.
*A01N 25/12* (2006.01)
*C09K 21/02* (2006.01)
*C09K 21/04* (2006.01)
*C04B 30/02* (2006.01)
*C04B 40/00* (2006.01)
*C04B 103/63* (2006.01)
*C04B 111/20* (2006.01)
*C04B 111/28* (2006.01)

(52) U.S. Cl.
CPC ............... *A01N 25/12* (2013.01); *C04B 30/02* (2013.01); *C04B 40/0042* (2013.01); *C09K 21/04* (2013.01); *C04B 2103/63* (2013.01); *C04B 2111/2092* (2013.01); *C04B 2111/28* (2013.01); *Y02W 30/97* (2015.05)

(58) Field of Classification Search
None
See application file for complete search history.

(56) References Cited

U.S. PATENT DOCUMENTS

| | | | |
|---|---|---|---|
| 2,881,138 A | 4/1959 | Reiss | |
| 3,621,917 A * | 11/1971 | Rosen | A62D 1/0071 169/44 |
| 3,799,738 A * | 3/1974 | Wagner | D06M 15/667 427/341 |
| 3,903,337 A | 9/1975 | Yamamoto et al. | |
| 4,038,451 A | 7/1977 | Brown et al. | |
| 4,182,681 A | 1/1980 | Gumbert | |
| 4,251,579 A | 2/1981 | Lee et al. | |
| 4,810,741 A | 3/1989 | Kim | |
| 4,909,328 A | 3/1990 | DeChant et al. | |
| 4,994,113 A | 2/1991 | Helmstetter | |
| 5,833,874 A | 11/1998 | Stewart et al. | |
| 6,576,289 B2 * | 6/2003 | Sosebee | B09B 3/00 252/601 |
| 7,045,476 B1 | 5/2006 | Lally | |
| 2007/0068685 A1 * | 3/2007 | Arnott | A62C 3/06 169/47 |
| 2008/0210444 A1 * | 9/2008 | Mulukutla | A62D 1/0007 169/47 |
| 2009/0320717 A1 | 12/2009 | Adams | |
| 2011/0005780 A1 * | 1/2011 | Rennie | A62C 3/07 169/9 |
| 2013/0092865 A1 * | 4/2013 | Carlson | A62D 1/0007 252/3 |

FOREIGN PATENT DOCUMENTS

| | | |
|---|---|---|
| EP | 0543349 A1 | 5/1993 |
| JP | 49-33880 B | 9/1974 |
| JP | 61-05856 A | 1/1986 |
| RU | 2216371 C2 | 11/2003 |
| RU | 2370295 C2 | 10/2009 |
| WO | WO 91/00326 A1 | 1/1991 |
| WO | WO 2009135973 A1 | 11/2009 |
| WO | WO 2014/001417 | 1/2014 |

OTHER PUBLICATIONS

U.S. Appl. No. 14/419,274, Jean-Philippe Pascal, filed Dec. 22, 2014.
[Author Unknown]—"CIMA Technical Bulletin #1, Cellulose insulation: codes, regulations, and specifications", 1998, The Cellulose Insulation Manufacturers Association, Dayton, OH, US, Dec. 1998; 5 pgs; accessed online on Apr. 9, 2013 at http://www.cellulose.org/userdocs/TechnicalSpecifications/CIMA-TechnicalBulletin01.pdf.
[Author Unknown]—Neobor® Product Data Sheet, "$Na_2B_4O_7 5H_2O$ Sodium Tetraborate Pentahydrate, Borax 5 Mol, Neobor Pentahydrate Borax, Technical Grade: Granular and Powder", Dec. 2007, Rio Tinto Minerals, 3 pgs; accessed online on Apr. 10, 2013 at http://www.borax.com/docs/product_pdfs_data/pds-borates-neobor.pdf?sfyrsn=1.
Shirtliffe, C.J., et al.—"Blown Cellulose Fiber Thermal Insulations: Part 2—Thermal Resistance" 1978, Thermal Transmission Measurements of Insulation, ASTM Special Technical Publication 660, pp. 104-129; 29 pgs.
Lacasse, K. et al: 2004, Book: "*Textile Chemicals. Environmental Data and Facts*", Publisher Springer, Section 6.4.8, Finishing with flame retardants pp. 425-443 (19 pages).
Carr, C., May 31, 1995, Book "*Chemistry of the Textiles Industry*". Springer Science & Business Media, section 3.6.3, pp. 112-113 (2 pages).

* cited by examiner

*Primary Examiner* — Joseph D Anthony
(74) *Attorney, Agent, or Firm* — Beatrice C. Ortego

(57) ABSTRACT

Fire-retardant powder comprising at least 30% by weight of Lewis acid, at least 5% by weight of alkaline bicarbonate, and at least 3% by weight of silica, and method of manufacturing such fire-retardant powder. A building material preferably comprising natural fibers and comprising at least 5% by weight and at most 30% of such powder.

20 Claims, No Drawings

FUNGICIDAL AND PARASITICIDAL FIRE-RETARDANT POWDER

CROSS-REFERENCE TO RELATED APPLICATIONS

The present application is a U.S. national stage entry under 35 U.S.C.§371 of International Application No. PCT/EP2011/073815 filed Dec. 22, 2011, which claims the priority benefit to French Patent application No. 10,61057 filed on Dec. 22, 2010, the whole content of this application being herein incorporated by reference for all purposes.

TECHNICAL FIELD OF THE INVENTION

The invention relates to a fire-retardant powder. It relates more particularly to a fungicidal and parasiticidal fire-retardant powder that can be used in building materials, in particular building materials based on natural fibres. It also relates to building materials containing this fire-retardant powder.

The expression "fire-retardant powder" is understood to mean a powder which, used in combination with an inflammable material, makes it possible to slow down or even inhibit the combustion of the inflammable material as measured for example by the EN ISO 11925-2 standard.

The expression "fungicidal powder" is understood to mean a powder in contact with which fungi and moulds (fungi such as *Aspergillus* in particular *Aspergillus fumigatus* and *Aspergillus niger*, *Cladosporium* in particular *Cladosporium fulvum* and *Cladosporium sphaerospermum*, *Penicilliums* in particular *Penicillium brevicompactum* and *Penicillium alteraria*), which have a tendency to grow in building materials, in particular on natural fibres, cannot survive.

The expression "parasiticidal powder" is understood to mean a powder in contact with which parasites (arthropods such as darkling beetles, weevils, lice, fleas, acarids, and xylophagous insects such as mites, longhorn beetles, termites), which have a tendency to grow in building materials, in particular on natural fibres, cannot survive. The parasites may be in the egg, larval or adult stage.

The action of the powder as fungicide or parasiticide may be direct. It may also be indirect, for example when the powder destroys a substance necessary to the survival of the fungus or parasite.

The expression "natural fibre" is understood to mean a fibre:
of plant origin such as flax, flax shives, hemp, stalk of peeled hemp, jute, sisal, coir, cotton, and wood,
or of animal origin such as wool, and feather.

The natural fibre may be virgin (first use) or recycled such as for example cotton (used clothing), or cellulose (old papers, boards), etc.

BACKGROUND OF THE INVENTION

The combustible behaviour of building materials containing natural fibres is a well-known problem that has existed for a very long time. Indeed, since wood and cob have a low fire resistance, man has developed alternative building materials mainly made of mineral materials such as stones, clay bricks, concrete, and mineral wools that are less combustible. However, the carbon footprint of such structures is high, on the one hand due to the energy needed for the production of such materials (such as cements, bricks, blocks, rock wools), and on the other hand due to the energy cost of transporting such reputedly heavy and dense materials from their production sites to the building sites where they are used.

By signing the Kyoto agreements, many countries are committed to reducing their greenhouse gas emissions by a factor of four between now and 2050. Thus, for example, European Directives henceforth impose energy consumption limits on new buildings. These energy consumption limits take into account the entire life cycle of the building: namely, the energy for producing the building materials, the energy for transporting them, the energy for assembling them, the energy consumption for heating (winter) and cooling (summer) the premises, the energy for the demolition of the building and the treatment and transport of the corresponding waste.

Thus, there are many architects and building designers who wish to use greater quantities of novel building materials comprising fibres of natural origin within the context of sustainable development. Indeed, these novel materials have an intrinsic carbon dioxide storage capacity since they are made up of a high percentage of organic matter. Moreover, these novel materials generally use little energy for their manufacture, they are light, they have a low heat capacity and they can have excellent thermal or sound insulation properties when they are used in a sufficient thickness. Their energy balance and their greenhouse gas footprint, per square meter built, are thus highly favourable over the life cycle of the building.

However, their combustible property is a curb on their use for obvious reasons of occupational safety of the premises, and their biodegradable property, attractive for the sustainable development aspect, poses serious problems with respect to the sensitivity of these materials to attacks by parasites and moulds which often result in an accelerated degradation of the structure.

Moreover, the occupation of these building by people or animals also requires a neutrality of the materials used with respect to the allergy risks or health risks promoted for example by fungi, acarids and parasites such as fleas or ticks.

A large number of treatments are proposed in order to fireproof these novel materials comprising natural fibres. Mention may for example be made of: brominated compounds (such as polybrominated aromatic compounds, in particular decabromodiphenyl ether and tetrabromobisphenol), compounds based on boron salts (such as borates and in particular the hydrated salts of boric acid), phosphorus-containing compounds (such as, in particular, zinc phosphate, ammonium phosphate, and magnesium, zinc or zirconium polyphosphonates), nitrogen-containing compounds (such as ammonium sulphates and ammonium halides), salts of metal (aluminium, antimony, zinc) compounds.

U.S. Pat. No. 4,182,681 discloses a fire retardant composition in powder form consisting mainly of alkaline compounds such as borax (hydrated $Na_2B_4O_7$) 43 w. % base of boric acid, Ammonium sulphate $((NH_4)_2SO_4)$ 31 w. %, Aluminium sulphate $(Al_2(SO_4)_3)$ 19 w. %, alkaline Sodium carbonate $(Na_2CO_3)$ 4 w %, Silica gel 1.3 w. %.

US2009/320717 discloses an alkaline fire retardant composition comprising a carbonate salt (alkaline) and one additional salt such as Borax $(Na_2B_4O_7.5H_2O)$ (also alkaline). The composition may comprise white sand along with Borax and Baking soda (example 2 respectively 40/40/20 parts, example 3 respectively 25/25/50 parts).

However, several of these fire-retardant compounds may present risks to the health of people handling these products during the manufacture of the building materials or to the health of the occupants of the buildings constructed with these compounds, or during the end-of-life treatment and recycling of the materials. Mention may for example be made of:

- among the fire retardants based on boric acid and boron salts certain national or even regional regulations (for example of the European Union) are changing to a CMR (carcinogenic, mutagenic and reprotoxic) classification of these substances,
- among brominated fire retardants: certain polybromobiphenyls or polybrominated diphenylethers which are the subject of regulatory restrictions in several regions of the world, moreover, the halogenated agents that generate acidic hydrogen halide fumes in the event of the thermal reutilization, as fuel, of the materials at the end of the life cycle,
- among the metal compounds, heavy metals (i.e. those capable of forming insoluble sulphides when they are in oxidized form in the form of cations) may be volatilized in the combustion fumes during the reutilization, as fuel, of the materials at the end of the life cycle. These combustion fumes must then be treated, for example with activated carbon to lower their heavy metal contents so that the fumes can be discharged into the natural environment with no environmental risk.

Among the components used as fungicide, mention may be made of: organotin compounds, organometallic complexes, or the (ammonium, copper, zinc, etc.) salts of organic acids, sulphur-containing compounds (such as octylisothiazolinone).

Among the parasiticidal compounds, mention may be made of pyrethrins, set of natural substances derived from pyrethrum flowers, synthetic pyrethroids, benzoylureas, organophosphorus compounds and carbamates. These substances have the drawback of being neurotoxic both to parasites and to humans. These compounds should therefore be used with precaution in order to minimize the risks to the health of the staff manufacturing the treated materials, or the building construction staff, or the people occupying buildings comprising materials treated with such compounds.

SUMMARY OF THE INVENTION

These drawbacks are lessened or eliminated by the use of the fire-retardant powder according to the present invention. The invention is based on the novel concept of producing a "3-in-1" (fire-retardant, fungicidal, and parasiticidal) protective fire-retardant powder that has a long-lasting fire-retardant, fungicidal and parasiticidal efficacy, that is healthy for humans, and is environmentally friendly, by reducing the bio-impacts in all stages of the life cycle of materials comprising such a powder: both in their manufacturing phase and in the material utilization phases and also at the end of the cycle at end-of-life of the material.

Indeed, it has surprisingly been observed that a Lewis acid could be mixed with a base of the alkaline bicarbonate type without neutralizing the fire-retardant properties of the acid and while retaining the fungicidal and parasiticidal properties of the alkaline bicarbonate.

Consequently, the invention relates to a fire-retardant powder comprising at least 30% by weight of Lewis acid, at least 5% by weight of alkaline bicarbonate and at least 3% by weight of silica.

A first advantage of the powder according to the present invention is that it simultaneously exhibits fire-retardant, fungicidal and parasiticidal properties.

A second advantage of the powder according to the present invention is that it does not contain compounds capable of degrading the air quality of buildings utilizing building materials that contain this powder.

A third advantage of the powder according to the present invention is that it minimizes the fume emission in the event of partial combustion of the building material that contains it.

A fourth advantage of the powder according to the present invention is that at least two of its major components (the alkaline bicarbonate and the silica) are not classified as chemically toxic to humans or animals.

A fifth advantage of the powder according to the present invention is that, due to the presence of the alkaline bicarbonate, it minimizes the emission of odours of certain natural materials such as those comprising feathers and wool.

A sixth advantage of the powder according to the present invention is that, in the event of water leaching of the building material that contains it, during its life cycle, for example during the dismantling of the structure, certain major components such as the alkaline bicarbonate and the silica, or even all of the components, for example when the Lewis acid is chosen from food-grade salts, have a minimal impact in the natural environment: in particular the bicarbonate is a natural pH buffer, and the silica is a component that is widespread in nature. Furthermore, during the hydrolysis of the Lewis acid in the presence of water, the acidic chemical species discharged, according to Brönsted, are partially neutralized by the alkalinity of the sodium bicarbonate.

A seventh advantage of the powder according to the present invention is that, in the event of energy recovery from the building material at the end of its usage cycle, as a mixture for example with other combustible natural compounds, a portion of the major components (alkaline bicarbonate and silica) will release into the fumes only $CO_2$ and water originating from the thermal decomposition. Moreover, the presence of an alkaline bicarbonate will reduce the emission of highly acidic gases (for example $SO_3$, $SO_2$, HF, HCl, HBr, NOx, $P_2O_5$, etc.) if the building material comprises sulphur-containing materials, halides-containing materials, nitrogen-containing materials or phosphate-containing materials.

DESCRIPTION OF THE PREFERRED EMBODIMENTS

In the powder according to the invention the Lewis acid is an acid according to the definition by Lewis, i.e. it is a chemical substance which can employ an electron lone pair from another molecule in completing the stable group of one of its own atoms. Therefore this renders it capable of accepting an electron pair, and therefore of creating a covalent bond with a Lewis base. Thus $H^+$ for instance is a Lewis acid since it can accept a lone pair, completing its stable form which requires two electrons.

Lewis acids such as phosphorus salts, in particular ammonium acid phosphates and alkaline acid phosphates are particularly suitable.

In the powder according to the invention, the alkaline bicarbonate may, for example, be bicarbonate in the strict sense such as potassium bicarbonate, sodium bicarbonate or ammonium bicarbonate. However, in this document it also covers compound salts such as alkaline sesquicarbonates (for example trona) which comprise bicarbonate and that presents a pH of at most 9.9, preferably at most 9.8 in water when at 0.1 mol/L concentration. Sodium or potassium bicarbonates or trona are especially suitable. Bicarbonates in the strict sense are recommended. Potassium bicarbonate or sodium bicarbonate, more particularly sodium bicarbonate, are preferred.

In the powder according to the invention, the silica may, for example, be silica in the strict sense such as anhydrous or hydrated silicon oxide, synthetic precipitated or pyrogenic silica. However, in this document it also covers silica compounds such as acid or alkaline silicates (such as sodium silicate, or sodium metasilicate), feldspars, diatomaceous earths, zeolites, phonolite, aluminium, magnesium or iron silicates, fuller's earth, talc ($Mg_3Si_4O_{10}(OH)_2$), mica, vermiculite, clays such as attapulgite (($Mg,Al)_2Si_4O_{10}(OH).4(H_2O)$), bentonite, montmorillonite, kaolin ($Al_2Si_2O_5(OH)_4$).

Precipitated silica and the phonolites are especially suitable. Amorphous (non-crystalline) silicas are recommended.

The powder comprises at least 30%, advantageously at least 40%, more advantageously at least 50% by weight of a Lewis acid such as monoammonium dihydrogen phosphate. Generally, the powder comprises at most 95%, advantageously at most 85%, more advantageously at most 70% by weight of Lewis acid.

The powder comprises at least 5% advantageously at least 10%, preferably at least 20% by weight of alkaline bicarbonate. Generally, the powder comprises at most 77%, advantageously at most 60%, more advantageously at most 40% by weight of alkaline bicarbonate.

In a certain embodiment of the invention, the powder comprises at least 20% and at most 40% by weight of alkaline bicarbonate.

In a certain other embodiment of the invention, the powder comprises at least 5% and less than 20% by weight of alkaline bicarbonate.

In one particularly preferred embodiment of the invention, the Lewis acid is constituted essentially of monoammonium dihydrogen phosphate.

The powder comprises at least 3% by weight of silica.

In a first particular embodiment the powder comprises at least 3% preferably at least 4%, more preferably at least 5% by weight of silica. In this first particular embodiment, the powder comprises generally less than 10%, preferably less than 9%, more preferably less than 8% weight of silica. In a special embodiment of the first particular embodiment of the invention, the powder comprises at least 3% and less than 10% by weight of silica.

In a second particular embodiment the powder comprises at least 10% by weight of silica, advantageously at least 15%, more advantageously at least 20%, preferably at least 25% by weight of silica. In this second particular embodiment the powder comprises generally at most 40%, advantageously at most 35%, more advantageously at most 30% by weight of silica. In a special embodiment of the second particular embodiment of the invention, the powder comprises at least 20% and at most 30% by weight of silica.

In order to be free flowing, and to limit the reaction of the Lewis acid with the alkaline bicarbonate, the powder of present invention should have a limited content of water. The water content of the powder according present invention is advantageously at most 15 w. %, preferably at most 10 w. %, more preferably at most 5 w %, most preferred at most 3 w %. This enables also to limit the reaction of Lewis acid with the alkaline bicarbonates. In particular the water content that is caught by crystalline compounds or salts is not detrimental as far as the water is not released by melting of the crystals up to 70° C.

According to one variant of the invention, the remainder of the powder according to the present invention comprises another fire-retardant constituent chosen from Lewis acids, boron salts, metal hydroxides, in particular aluminium hydroxides, alkaline-earth metal hydroxides, in particular magnesium hydroxide, anhydrous or hydrated zinc sulphates, ammonium sulphates, anhydrous or hydrated magnesium sulphates, calcium sulphate (gypsum), phosphorus salts, and mixtures thereof. In one preferred variant, the fire-retardant powder is essentially free of boron salts and/or boron acid. Indeed boric acid and boron compounds are classified as reprotoxic for humans. One should understand by essentially free of boron salts or of boric acid, a fire-retardant powder without intended boron compounds added other than the natural boron content traces of the added compounds. In this case, the boron content expressed as Boron (B) should be less than 2 w %, preferably less than 1 w %, more preferably less than 0.1 w % of the fire-retardant powder.

In one advantageous variant, the fire-retardant powder is free of other fire-retardant constituents capable of forming nitrogenous and/or potash fertilizers favourable to the growth of fungi and moulds.

According to another variant of the invention, the fire-retardant powder is even free of any other fire-retardant constituent.

In another variant, the powder is free of other fungicidal constituents.

In a preferred variant, the powder is free of neurotoxic parasiticidal active principles. And in a more preferred variant, the powder is free of other parasiticidal active principles.

In another advantageous variant, the fire-retardant powder does not comprise any constituent other than the ammonium or alkaline acid phosphate, the alkaline bicarbonate, and the silica.

In a particularly advantageous variant, the fire-retardant powder does not comprise any constituent other than monoammonium dihydrogen phosphate, sodium bicarbonate, and the silica.

The Lewis acid, bicarbonate and silica mixture must be as homogeneous as possible. It is recommended that the particle sizes of the Lewis acid, bicarbonate and silica be similar in order to facilitate the mixing. The mixing may be carried out in any type of powder mixer known to those skilled in the art, such as blade mixers equipped with lifter blades. However, it has been observed that in certain circumstances, in particular when the mixing is carried out in ploughshare mixers, which is advantageous, too long a mixing time may lead to a loss of efficacy of the fire-retardant powder. In general, times longer than 10 minutes should be avoided. Generally, it is also recommended to mix the Lewis acid, bicarbonate and silica mixture in such a way as to fluidize it. This fluidization takes place in a ploughshare mixer when the mixture falls back into the mixer following the rotation of the ploughshare.

The powder according to the invention, comprising a large portion or even a major portion by weight of constituents that are non-toxic to humans or animals, may be readily used in a large number of building materials, advantageously in building materials comprising natural fibres chosen from virgin or recycled fibres of plant origin such as flax, flax shives, hemp, stalk of peeled hemp, jute, sisal, coir, cotton, and wood, or of animal origin such as wool, and feather.

The powder according to the invention is advantageously used in the manufacture of material comprising cellulose wadding.

Another aspect of the invention relates to the use of a powder according to the invention for its combined fire-retardant, fungicidal and parasiticidal effects.

Fibres to which the powder according to the present invention has been added may be used alone, for example in the form of loose-fill insulation or as a mixture with natural mineral mortars, or as a mixture with binders of, preferably natural, adhesive type before web formation and compaction, or as a mixture with plastics, preferably bioplastics such as polylactic acid (PLA), polyhydroxybutyrate (PHB), polyamide 11 derived from plant oil, bio-derived polyethylene (PE), bio-derived polyvinyl chloride (PVC), and composite mixtures thereof.

In a first particular embodiment, at least one of the components of the powder according to the present invention, preferably at least two components, more preferably still at least three components chosen from the Lewis acid, the alkaline bicarbonate, and the silica is (are) present in the form of particles having a weight-average diameter less than or equal to 100 µm, preferably less than or equal to 80 µm, more preferably still less than or equal to 30 µm. The diameters are measured by laser diffraction and diffusion particle size analysis on a Malvern Mastersizer S particle size analyser via the liquid route, using an He—Ne laser source having a wavelength of 632.8 nm and a diameter of 18 mm, a measurement cell equipped with a backscatter 300 mm focal length (300 RF), an MS 17 liquid preparation unit, an automatic solvent filtration kit ("ethanol kit") using ethanol saturated with bicarbonate, according to the ISO 13320-2009 standard. The particle size distribution is that calculated as the volume distribution of the particles. This volume distribution is equivalent to a weight distribution for a given particle density.

According to one advantageous embodiment of the present invention, the manufacture of the powder comprises at least one step of simultaneous milling of at least two of the components of the powder chosen from the Lewis acid, the alkaline bicarbonate, and the silica. The co-milling of at least the alkaline bicarbonate and the silica is preferred. This co-milling makes possible an especially increased efficacy of the fire-retardant, fungicidal and parasiticidal properties. This co-milling phase may be carried out in any mill known to those skilled in the art, such as grinding mills, impact plate mills, hammer mills or pin mills. Pin mills are advantageous. Mills equipped with particle size selectors, which allow the internal recycling to the mill of the largest particles, are particularly advantageous.

In a second particular embodiment, at least one of the components of the powder according to the invention, preferably at least two components, more preferably still at least three components chosen from the Lewis acid, the alkaline bicarbonate, and the silica is (are) present in the form of particles having a weight-average diameter of at least 80 µm, preferably of at least 100 µm, more preferably still of at least 130 µm, and at most 500 µm, preferably at most 400 µm and more preferably still 300 µm. The diameters of the powder of this second particular embodiment are measured by screening through a sieve according to the ISO 3310-1:2000 standard. This particular embodiment allows easier processing in the case of the production of building materials comprising constituents, in particular natural fibres, which may be co-milled with the fire-retardant powder. This co-milling phase allows excellent mixing of the powder with the material while limiting the entrainment of the powder particles into the dust extraction devices placed level with and downstream of the mill.

Consequently, the present invention also relates to a method of manufacturing building material comprising virgin and/or recycled natural fibres and a powder according to the invention, the manufacturing method comprising a step of simultaneous milling of the natural fibres and of the powder according to the present invention.

In general, the building material using the powder according to the present invention comprises at least 5% by weight, advantageously at least 10%, and more advantageously at least 13% of powder. In the case of a building material comprising for example natural fibres, it is not desirable for the material to comprise too large an amount of powder according to the present invention. Preferably the building material comprises at most 30% by weight, advantageously at most 20%, and more advantageously at most 17% of powder.

Consequently, the present invention also relates to a building material preferably comprising natural fibres and comprising the powder of the present invention.

The following examples are intended only to exemplify the invention and are not intended to limit the scope of the claimed invention.

EXAMPLES

Example 1 (Powder in Accordance with the Invention)

2 kg of monoammonium dihydrogen phosphate, 1 kg of Solvay Bicar 13/27 sodium bicarbonate and 1 kg of silica of Hauri MOS 500 phonolite type are taken.

Using three devices for metering solids by weight, the three powders are introduced simultaneously into an Alpine UPZ 100 pin mill rotating at 17 000 rpm at a respective throughput of 2, 1 and 1 kg/h of each powder.

A homogeneous powder is obtained comprising 50% by weight of monoammonium dihydrogen phosphate, 25% by weight of sodium bicarbonate and 25% by weight of silica.

The particle size of the powder is such that the weight-average diameter is less than or equal to 80 µm.

Example 2 (In Accordance with the Invention)

In this example, tests are carried out on various strains of pathogenic fungi of the human habitat (*Aspergillus niger, Cladosporium phaerospermum, Penicillium brevicompactum*) or lignivorous fungi (dry rot: *Serpula lacrymans*) in order to evaluate the fungicidal efficacy of the powder according to the present invention. For this purpose, the powder according to Example 1 was deposited directly on an agar medium inoculated with one of the following strains: *Aspergillus niger, Cladosporium sphaerospermum, Penicillium brevicompactum*, and *Serpula lacrymans*. The areas of inhibition, that is to say the areas where the growth of the fungi was stopped by the action of the powder, are very pronounced for each of the strains used.

Example 3 (In Accordance with the Invention)

Larvae of common European termites (*Reticulitermes lucifugus*), which are xylophagous insects, are used in order to evaluate the insecticidal efficacy of the powder according to the present invention. For this purpose, the powder according to Example 1 was mixed with cellulose fibres.

Two powder doses are tested: 10% and 15% in the cellulose fibres. The mortality of *Reticulitermes lucifugus* is observed as a function of the time.

Example 4 (In Accordance with the Invention)

Larvae of clothes moths (*Tineola bisselliella*), which are keratophagous insects, are used in order to evaluate the insecticidal efficacy of the powder according to the present invention. For this purpose, the powder according to Example 1 was mixed with hemp fibres. Two powder doses are tested: 10% and 15% by weight mixed in the hemp fibres. The mortality of *Tineola bisselliella* is observed as a function of the time.

Example 5 (In Accordance with the Invention)

Manufacture of insulating cellulose wadding.

100 kg of old newspapers are taken. After sorting (removal of metals and plastics), the paper is milled in a first mill in order to shred the paper and reduce it to pieces the size of a postage stamp.

Using two solids metering devices (calibrated screw feeder) each equipped with a buffer hopper, the following:

a powder composed of a mixture of monoammonium dihydrogen phosphate (composed of particles having a weight-average diameter between 80 and 200 µm), Solvay Bicar 13/27 sodium bicarbonate (screened between two sieves of 130 µm and 270 µm) and silica of Hauri MOS 500 phonolite type, and the paper shredded in the first step reduced to pieces the size of a postage stamp, are introduced simultaneously into a second mill.

The second mill is placed just after the addition of the powder of additives.

The pieces of paper previously shredded and the powder added in a proportion of 15% by weight relative to the total mixture (powder plus paper) are finely and simultaneously reduced.

At the outlet of the mill, a fibre with a fluffy appearance is obtained that has many asperities and is soft to the touch, with good fixation and good homogeneity of the powder in the fibres. Its bulk density is 35 kg/m$^3$. Its thermal conductivity is around 0.038 W.m$^{-1}$.K$^{-1}$. Its specific heat capacity is around 1650 J/(kg.K).

A filtration system that enables the paper dust to be recovered makes it possible to verify that the initial powder is not entrained very much into the dust extraction circuits.

At the outlet of the second mill, the treated wadding is then weighed and compressed before being bagged.

The cellulose wadding thus treated is then used as thermal insulation in insulation thicknesses of 5 to 45 cm.

The amounts used are dependent on the installation techniques: by pneumatic blowing into wall compartments: 50 to 65 kg/m$^3$, by wet spraying: 30-50 kg/m$^3$, and by manual installation into wall compartments: 50-65 kg/m$^3$.

This additive-laden wadding has good resistance to fire, and to the growth of fungi and parasites.

Example 6

Comparison of the fire-retardant behaviour of various compositions in accordance or not with the present invention.

Various powder compositions using the same equipment and same operating conditions as Example 1 were used, using the raw materials listed at table 1.

In this series of tests, a virgin cellulose wadding was taken such as that described in Example 5, obtained by defiberizing in a UPZ 100 pin mill rotating at 7000 rpm.

The fire behaviour of the various formulations has been evaluated in a comparative manner according to a methodology adapted from the NF EN ISO 11925-2 standard: Reaction to fire—Ignitability of building products subjected to direct impingement of flame—Part 2: Single-flame source test.

A flame from a gas burner ref. X2000PZ (Soudogaz) of 12 cm long wherein the internal blue part of the flame is set to 4 cm, is applied to the face of the material to be tested with an angle of 45° and at a distance of 2 cm from the end of the blue part of the flame to the tested material. After 5 seconds of flame exposition to the material, the burner is withdrawn, and a visual observation determines if there is ignition of the cellulose wadding, the time that the flame lasts for of the cellulose wadding (flame duration), the duration of burning (persistence of the zone of incandescence), and the surface area of the spread of the fire in % of the cellulose wadding. The results are moreover interpreted according to the observations made during the test on the nature of the burning (in particular whether it is deeply burned towards the thickness of the cellulose waddings, or superficially burned, or slightly superficially burned).

The comparative fire-retardant behaviours of the various compositions powders tested in cellulose wadding are given at table 2 (powder compositions not conform to present invention) and at table 3 (powder compositions conform to present invention).

One can see in table 3, tests 6.7 to 6.14 results using powder compositions conform to the present invention, that the surface area of the spread fire is at most 90%, and more often at most 60%; and, according the composition and the quantity of fire-retardant powder, only superficial burned cellulose waddings (tests 6.10 to 6.14).

In comparison, the tests performed with non-conform fire retardant powders in tests 6.1 to 6.6 (table 2), the surface area of spread fire ranges from 90% to 100% with deeply burned cellulose wadding in all cases.

Example 7

A comparative test has been done to compare the flame retardant compositions known in the previous art using boric acid alkaline derivatives such as sodium borax. For this a disclosed composition in U.S. Pat. No. 4,182,681 (hereafter called US'681) which is non conform to present invention has been compared to a flame retardant composition conform to present invention.

The powder composition described in US'681 column 4 lines 5 to 11 consisted of: Borax, Ammonium sulphate, Aluminium sulphate, Soda Ash (sodium carbonate), Silica gel, and Diammonium phosphate, with weight percentages indicated at table 4 of the present document, was prepared by careful mixing in a laboratory Lödige plough mixer during 2 minutes. In order to activate the powder composition as taught by US'681, the cellulose fibers were preheated at 90° C. before being grinded with the fire retardant composition powder in same equipments of example 6 and same operating conditions, with a 20 w. % content of the fire-retardant powder reported to the treated cellulose wadding.

This treated cellulose wadding was compared with a cellulose wadding treated with 20% in weight (reported to total final weight of treated cellulose) of a powder conform to the present invention, consisting of Mono-ammonium phosphate (Lewis acid), Sodium bicarbonate, Silica (Vulkanit). The chemicals compounds were first carefully mixed in a laboratory Lödige plough mixer during 2 minutes. Then the cellulose wadding was grinded with the obtained fire retardant composition powder in same equipments and operating conditions of example 6, with a 20 w. % content of the fire-retardant powder reported to the treated cellulose wadding.

Each tests of examples 7.a (US'681 non conform) and 7.b (conform) were repeated twice and results are given at table 6.

One can see from results at table 6 that the flame duration of cellulose wadding are comparable in both cases with values of 0.5 s. But post flame burning duration (incandescent cellulose without flame) is much higher (45 and 22 seconds) with non-conform fire-retardant, compared to short post flame burning durations (5 and 7 seconds) with conform fire-retardant. Also the loss of weight of the burned treated cellulose is less (2.2% versus 3.5%) with the conform composition compared to the non-conformed composition.

Moreover the non-conform composition from example 7.a needs an activation step of the ammonium sulphate composition from US'681. Indeed two tests completed as example 7.a (non conform) but without pre-heating the cellulose to 90° C. before introducing the fire-retardant powder, leads to post flame burning duration (incandescent cellulose without flame) even higher of 2 minutes (120 s) to 14 minutes (840 s) and a loss of weight of the burned treated cellulose to up to 38%.

Comparatively the present invention powder gives better results on fire-retardant effects and with no specific need of thermal activation of the fire retardant powder, contrary to US'681 known art for instance.

Should the disclosure of any patent, patent applications, and publications that are incorporated herein by reference conflict with the present description to the extent that it might render a term unclear, the present description shall take precedence.

TABLE 1

Raw materials used for making flame retardant compositions from Example 6 and 7.

| Raw materials used | Chemical formula | From | Ref. and Comment |
|---|---|---|---|
| Mono ammonium Phosphate | $NH_4H_2PO_4$ | Thermphos | Food grade |
| Di ammonium phosphate | $(NH_4)_2HPO_4$ | VWR | Technical grade |
| Sodium Bicarbonate | $NaHCO_3$ | Solvay | Bicar 0/10 - 100% < 100 μm |
| Amorphous natural silica | — | Hauri | Vulkanite 500 |
| Amorphous silica | $SiO_2$ | Rhodia | Tixosil 38AB |
| Sodium carbonate | $Na_2CO_3$ | Solvay | Soda Solvay - Light soda ash |
| Ammonium sulphate | $(NH_4)SO_4$ | Merk | Size Fractions >800 μm 32%, 80 < F < 800 μm 68% |
| Aluminium sulphate | $Al_2O_{12}S_3 \cdot 18\,H_2O$ | Sigma-Aldrich | Size Fractions >800 μm 14%, 80 < F < 800 μm 14%, F < 80 μm 72% |
| Sodium Borax | $Na_2B_4O_7 \cdot 10\,H_2O$ | Merk | Size Fractions <150 μm 19%, 150 < F < 560 μm 42%, F > 560 μm 39% |

TABLE 2

Example 6 - Comparative fire-retardant behaviours of non conform compositions powders tested in cellulose wadding.

| Test nber # | Internal ref. | Conform to invention | Cellulose wadding plus fire retardant composition with weight fraction of the fire retardant composition reported to the total weight of treated cellulose wadding | flame duration s | duration of burning s | surface area of the spread of the fire % | comment | Qualitative ranking |
|---|---|---|---|---|---|---|---|---|
| 6.1 | 1 | No | cellulose wadding alone | 8 | 10 | 75 | deeply burned | Bad |
| 6.2 | 7 | No | 15% Sodium carbonate | 0.5 | 7 | 100 | deeply burned | Bad |
| 6.3 | 6 | No | 15% Sodium bicarbonate (bicar) | 1 | 8 | 95 | deeply burned | Bad |
| 6.4 | 14 | No | 10% Citric acid | 3 | 20 | 95 | deeply burned | Bad |
| 6.5 | 10 | No | 4% carbonate + 4% bicar + 4% vulkanit | 1 | 2 | 95 | deeply burned | Bad |
| 6.6 | 11 | No | 8% Hydroxyde d'aluminium + 4% bicar + 4% vulkanit | 1 | 6 | 90 | deeply burned | Bad |

TABLE 3

Example 6 - Comparative fire-retardant behaviours of conform compositions powders tested in cellulose wadding.

| Test nber # | Internal ref. | Conform to invention | Cellulose wadding plus fire retardant composition with weight fraction of the fire retardant composition reported to the total weight of treated cellulose wadding | flame duration s | duration of burning s | surface area of the spread of the fire % | comment | Qualitative ranking |
|---|---|---|---|---|---|---|---|---|
| 6.7 | 13 | Yes | 8.5% NH4H2PO4 + 1% bicar + 0.5% Tixosil 38AB | 0.5 | 10 | 90 | superficially burned | Insufficient |
| 6.8 | 17 | Yes | 4% NH4H2PO4 + 4% bicar + 4% vulkanite | 2 | 9 | 60 | deeply burned | Insufficient |
| 6.9 | 18 | Yes | 6% NH4H2PO4 + 4% bicar + 4% vulkanite | 2 | 5 | 60 | deeply burned | Insufficient |
| 6.10 | 29 | Yes | 8% NH4H2PO4 + 4% bicar + 4% vulkanite + 2% CaSO4, 2H2O | 6 | 1.5 | 50 | superficially burned | Correct |
| 6.11 | 16 | Yes | 8% NH4H2PO4 + 4% bicar + 4% vulkanite | 1 | 0.5 | 50 | superficially burned | Good |
| 6.12 | 25 | Yes | 8% NH4H2PO4 + 4% bicar + 4% vulkanite + 2% Na2O3SiO2, 3H2O (Na silicate) | 1 | 0.5 | 50 | superficially burned | Good |
| 6.13 | 19 | Yes | 8% NH4H2PO4 + 4% bicar + 4% vulkanite | 0 | 1 | 40 | superficially burned | Good |
| 6.14 | 27 | Yes | 8% NH4H2PO4 + 4% bicar + 4% vulkanite + 2% Na2SiO3•5H2O (Na metasilicate) | 3 | 0.45 | 33 | superficially burned | Good |

TABLE 4 fire-retardant powder composition of Examples 7.a (non-conform)

| Chemical | Percentage of fire-retardant powder composition % |
|---|---|
| Sodium Borax | 42.5 |
| Ammonium sulphate | 31.25 |
| Aluminium sulphate | 18.75 |
| Sodium carbonate | 4.375 |
| Silicagel | 1.25 |
| Di-ammonium phosphate | 1.875 |

TABLE 5 fire-retardant powder composition of Examples 7.b (conform)

| Chemical | Percentage of fire-retardant powder composition % |
|---|---|
| Mono-ammonium Phosphate | 62.5 |
| Sodium Bicarbonate | 18.75 |
| Silica (Vulkanite 500) | 18.75 |

TABLE 6

Example 7 - Comparative fire-retardant behaviours of non-conform compositions powders (US'681) and present invention powder tested in cellulose wadding.

| Test nber | Internal ref. | Conform to invention | Cellulose wadding plus fire retardant composition with weight fraction of the fire retardant composition reported to the total weight of treated cellulose wadding % | flame duration s | duration of burning s | surface area of the spread of the fire % | comment | losen weight of burned cellulose wadding after test % |
|---|---|---|---|---|---|---|---|---|
| 7.a | 3 | no | 20% of tab.4 composition (US'681) | 0.5 | 45 | 80 | superficially burned | 3.5 |
|  | 3 bis | no | 20% of tab.4 composition (US'681) | 0.5 | 22 | 80 | superficially burned | 3.5 |
| 7.b | 1 | yes | 20% of tab.5 composition | 0.5 | 5 | 80 | Slightly superficially burned | — |
|  | 1 bis | yes | 20% of tab.5 composition | 0.5 | 7 | 80 | Slightly superficially burned | 2.2 |

The invention claimed is:

1. A fire-retardant powder comprising at least 30% by weight of Lewis acid, at least 18.75% by weight of alkaline bicarbonate, and at least 18.75% by weight of a silica compound selected from the group consisting of silica, acid silicates, alkaline silicates, feldspars, diatomaceous earths, zeolites, phonolite, aluminium silicate, magnesium silicate, iron silicates, fuller's earth, talc, mica, vermiculite, clays, bentonite, montmorillonite, and kaolin.

2. The fire-retardant powder according to claim 1, wherein said alkaline bicarbonate is sodium bicarbonate.

3. The fire-retardant powder according to claim 1, comprising at most 15% by weight of water.

4. The fire-retardant powder according to claim 1, wherein said Lewis acid is mono-ammonium phosphate.

5. The fire-retardant powder according to claim 1, being essentially free of boron salts and/or boron acid.

6. The fire-retardant powder according to claim 1, being free of neurotoxic parasiticidal active principles.

7. The fire-retardant powder according to claim 1, wherein at least one of the components selected from the group consisting of said Lewis acid, said alkaline bicarbonate, and said silica compound is present in the form of particles having a weight-average diameter of at least 80 µm.

8. The fire-retardant powder according to claim 1, wherein at least one of the components selected from the group consisting of said Lewis acid, said alkaline bicarbonate, and said silica compound is present in the form of particles having a weight-average diameter of at most 100 µm.

9. A method of manufacturing the fire-retardant powder according to claim 8, comprising at least one step of simultaneous milling of at least two of the components of the powder selected from the group consisting of said Lewis acid, said alkaline bicarbonate, and said silica compound.

10. The fire-retardant powder according to claim 1, further being a fungicidal and parasiticidal powder.

11. A method for producing a building material, comprising using the fire-retardant powder according to claim 1 to make said building material.

12. A method for manufacturing the fire-retardant powder according to claim 1, comprising mixing said Lewis acid, said alkaline bicarbonate, and said silica compound, each of which being in the form of particles.

13. A building material comprising at least 5% by weight of the powder according to claim 1.

14. The building material according to claim 13, comprising at most 30% by weight of said powder.

15. A method of manufacturing a building material comprising the fire-retardant powder according to claim 1, and further comprising natural fibers, the manufacturing method comprising simultaneous milling said natural fibers and said powder.

16. The fire-retardant powder according to claim 3, comprising at most 10% by weight of water.

17. The fire-retardant powder according to claim 16, comprising at most 5% by weight of water.

18. The building material according to claim 13, comprising at least 10% by weight of said fire-retardant powder.

19. The building material according to claim 13, comprising at most 20% by weight of said fire-retardant powder.

20. The building material according to claim 13, further comprising natural fibers.

* * * * *